(12) United States Patent
Yoshida et al.

(10) Patent No.: US 7,354,727 B2
(45) Date of Patent: Apr. 8, 2008

(54) METHOD AND APPARATUS FOR CLASSIFYING B-LYMPHOCYTES

(75) Inventors: Ayumu Yoshida, Kobe (JP); Shimeru Kamihira, Nagasaki (JP)

(73) Assignee: Sysmex Corporation, Kobe-Shi (JP)

( * ) Notice: Subject to any disclaimer, the term of this patent is extended or adjusted under 35 U.S.C. 154(b) by 498 days.

(21) Appl. No.: 10/944,188

(22) Filed: Sep. 20, 2004

(65) Prior Publication Data

US 2005/0069959 A1   Mar. 31, 2005

(30) Foreign Application Priority Data

Sep. 26, 2003  (JP) .............................. 2003-336447

(51) Int. Cl.
*G01N 33/00*   (2006.01)
(52) U.S. Cl. ................ 435/7.24; 435/7.25; 435/372.2; 436/522; 436/17; 436/63; 436/64; 436/164; 422/68.1; 422/82.05; 422/82.09; 422/91

(58) Field of Classification Search ............... 435/7.24, 435/7.25, 372.2; 436/522, 17, 63, 64, 164; 422/68.1, 82.05, 82.09, 91
See application file for complete search history.

(56) References Cited

U.S. PATENT DOCUMENTS

| 4,284,412 A | * | 8/1981 | Hansen et al. ............. 435/7.24 |
| 4,987,086 A | | 1/1991 | Brosnan et al. |
| 5,648,225 A | * | 7/1997 | Kim et al. ................. 435/7.24 |

* cited by examiner

*Primary Examiner*—Gailene R. Gabel
(74) *Attorney, Agent, or Firm*—Birch, Stewart, Kolasch & Birch, LLP

(57) ABSTRACT

A B-lymphocyte classifying method includes the steps of (1) preparing a measurement sample by mixing a blood sample with a lysing reagent to lyse erythrocytes and to shrink the B-lymphocytes in the blood sample, (2) letting the measurement sample flow through a flow cell of a flow cytometer, (3) radiating a light beam onto a cell in the measurement sample that is flowing through the flow cell, (4) detecting at least two scattered light emitted from the irradiated cell, (5) specifying a region of a B-lymphocyte cluster in accordance with the detected scattered light, and (6) counting the number of B-lymphocytes in the specified region.

10 Claims, 5 Drawing Sheets

[Fig. 1]
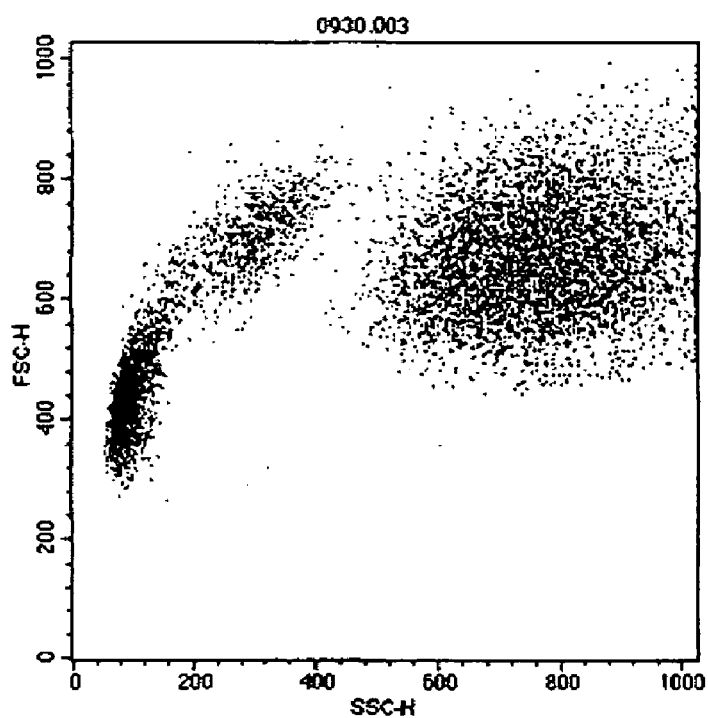
[Fig. 2]
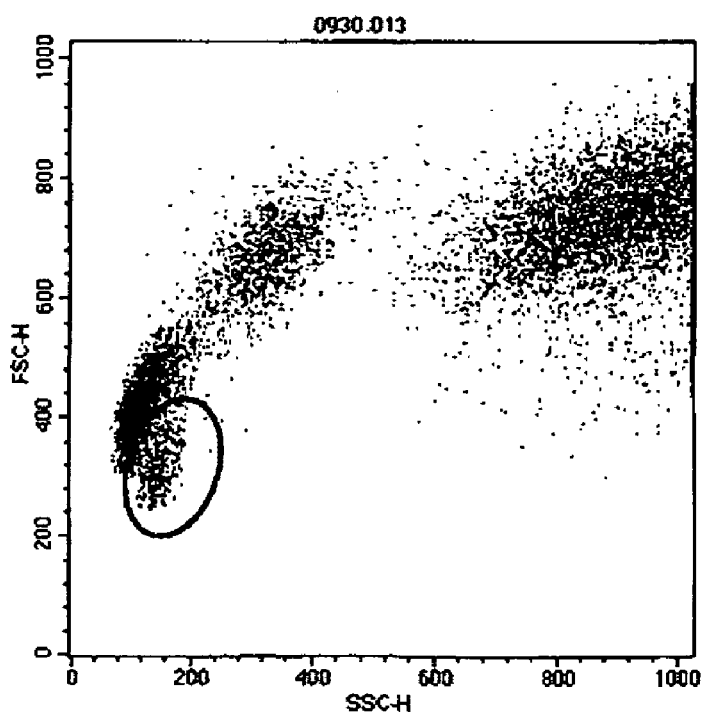

[Fig. 3]
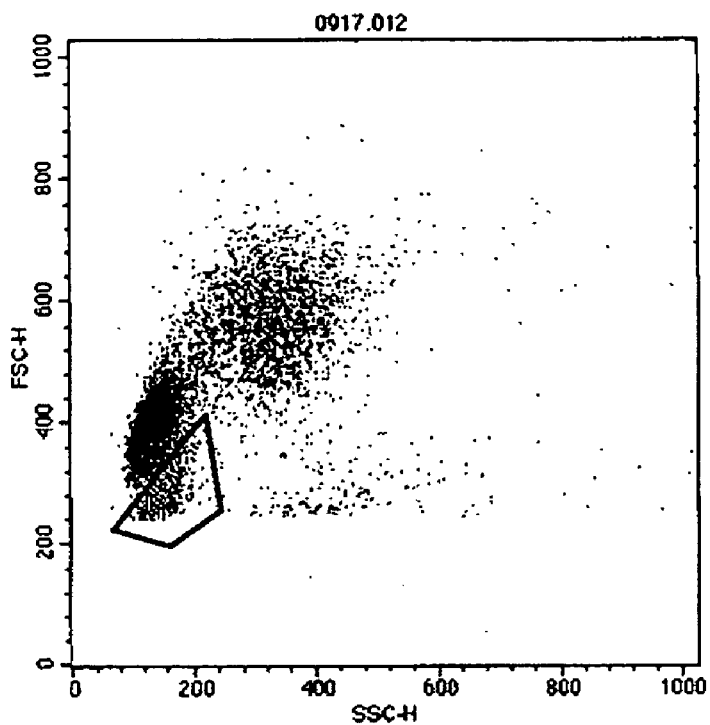
[Fig. 4]
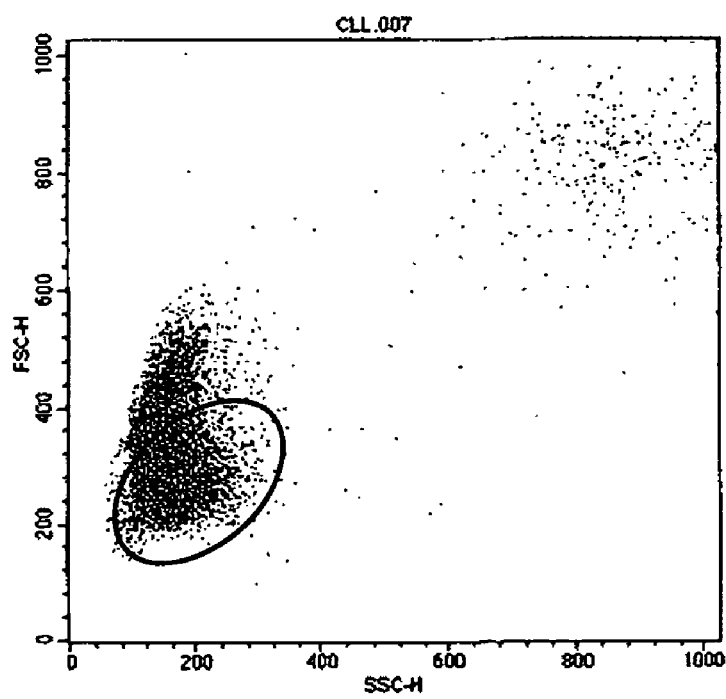

[Fig. 5]
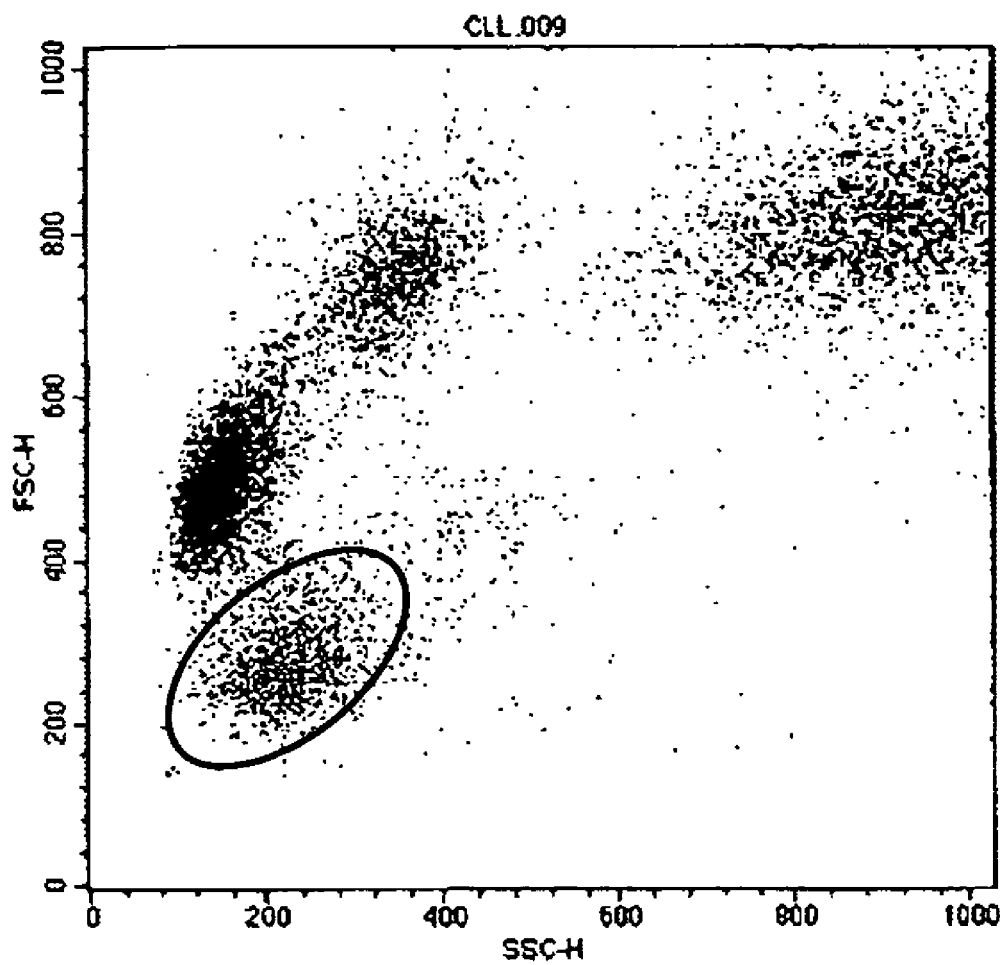

[Fig. 6]
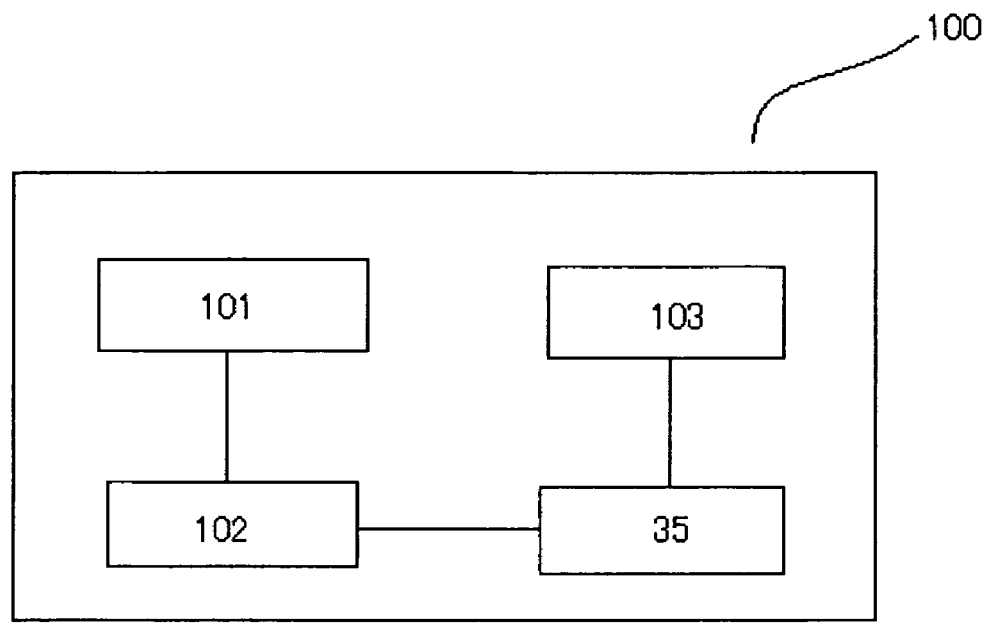

[Fig. 7]
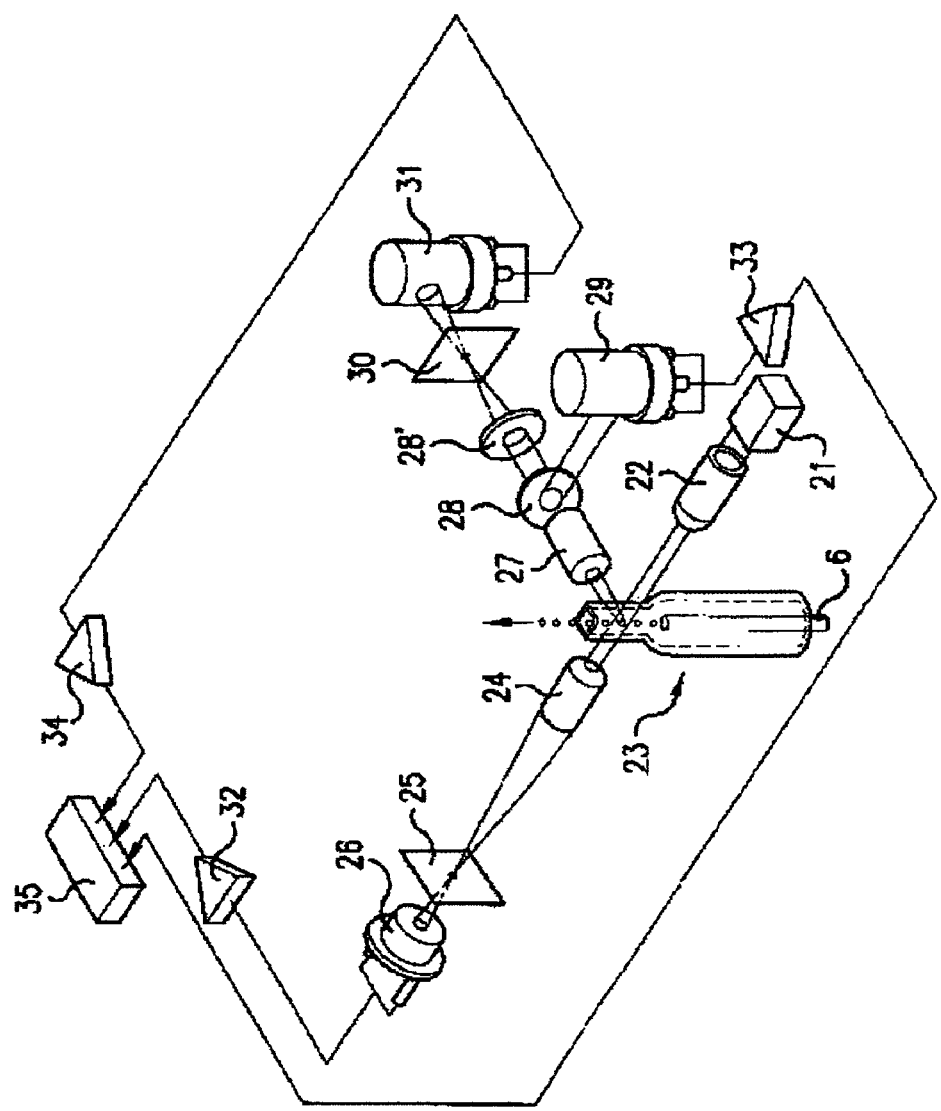

METHOD AND APPARATUS FOR CLASSIFYING B-LYMPHOCYTES

This Non-provisional application claims priority under 35 U.S.C. § 119(a) on patent application Ser. No. 2003-336447 filed in Japan on Sep. 26, 2003, the entire contents of which are hereby incorporated by reference.

BACKGROUND

The present invention relates to a method and an apparatus for classifying B-lymphocytes in a blood sample. The leukocytes in a peripheral blood of a healthy human being can be classified into lymphocytes, monocytes, neutrophils, eosinophils, and basophils. The lymphocytes are further roughly classified into three types called subsets (T-lymphocytes, B-lymphocytes, and NK-lymphocytes). The B-lymphocytes are lymphocytes derived from bone marrow and have immunoglobulin on the surface thereof. Further, the B-lymphocytes play a very important role in an immunity function of a human being such as production of antibodies by being differentiated into plasma cells. Usually, a B-lymphocyte ratio (%) is used to represent the ratio occupied by the B-lymphocytes in the total lymphocytes.

Since the B-lymphocytes are strongly involved in immunity mechanism, the increase or decrease thereof is directly linked to capturing the change in the immunity function. At ordinary times, the B-lymphocytes are present at a constant ratio; however, the ratio may change in accordance with the presence of a disease. Therefore, measurement of a B-lymphocyte ratio is useful in obtaining information on the presence of a disease.

Examples of the diseases showing increase in the B-lymphocytes include multiple myeloma, B-lymphocyte type chronic lymphocytic leukemia, infectious mononucleosis, Burkitt's lymphoma, and others. Examples of the diseases showing decrease in the B-lymphocytes include AIDS, progressive cancer, Hodgkin's lymphoma, agammaglobulinemia, measles, chicken pox, herpes, and others.

As a technique for classifying and counting lymphocytes, manual methods have often been used, such as the rosette method in which, by using the fact that sheep erythrocytes sensitized with a complement bind to B-lymphocytes, the number thereof is counted while the smear sample thereof is being observed with an optical microscope, or the surface immunity fluorescence method in which a smear sample of blood is labeled with a fluorescence-labeled antibody and the number of lymphocytes is counted while the smear sample is being observed with a fluorescence microscope. However, in recent years, a flow system is generally used in which blood cells labeled with a fluorescence-labeled antibody are let to flow in a liquid and the blood cells are classified and counted by performing signal processing on signals obtained from individual blood cells.

In a flow system, blood cells are let to flow in a liquid, and a signal is detected for each blood cell (for example, a signal based on the difference of optical characteristics). In doing this, by adding an antibody corresponding to the cells that should be detected after labeling the antibody with a fluorescent substance, only the cells that should be detected emit fluorescence signals, and information on the desired cells can be obtained by detecting these signals (See U.S. Pat. No. 4,284,412).

Antibodies have a property of binding only to a specific substance, and are known to have an extremely high specificity thereof. At present, substances (such as protein) appearing on specific cells are specified and, by using the antibodies that are prepared to bind to this substance, one can perform a fine classification of cells. Antibodies (for example, anti-CD19, anti-CD20 antibodies) that are used for classifying and counting B-lymphocytes are prepared to bind to a substance that appears only on B-lymphocytes.

The fluorescence-labeled antibodies to be used require an extremely high technique and time for preparation thereof, and also are very expensive though used in a slight amount.

Further, The flow system using the fluorescence-labeled antibodies requires a complex procedure for letting a slight amount of cells bind to a slight amount of fluorescence-labeled antibodies without loss for measurement, and requires repetition of short-time operations and a period of time for waiting.

SUMMARY

An object of the present invention is to provide an inexpensive and facilitated method of classifying B-lymphocytes.

A method for classifying B-lymphocytes according to the first aspect of the present invention includes the steps of:

(1) preparing a measurement sample by mixing a blood sample with a lysing reagent to lyse erythrocytes and to shrink B-lymphocytes in said blood sample;

(2) letting said measurement sample flow through a flow cell of a flow cytometer;

(3) radiating a light beam onto a cell in the measurement sample that is flowing through the flow cell;

(4) detecting at least two scattered light emitted from the irradiated cell;

(5) specifying a region of a B-lymphocyte cluster in accordance with the detected scattered light; and (6) counting the number of B-lymphocytes in the specified region.

An apparatus for classifying B-lymphocytes according to the second aspect of the present invention includes:

(1) a measurement sample preparing section for preparing a measurement sample by mixing a blood sample with a lysing reagent to lyse erythrocytes and to shrink B-lymphocytes in said blood sample;

(2) a flow cell for introducing said measurement sample;

(3) a light source for radiating a light beam onto a cell in the measurement sample that is flowing through the flow cell;

(4) a first scattered light detector and a second scattered light detector for detecting scattered light emitted from the irradiated cell;

(5) an analyzing section for specifying a region of a B-lymphocyte cluster in accordance with the detected scattered light and counting the number of B-lymphocytes in the specified region.

BRIEF DESCRIPTION OF THE DRAWINGS

FIG. 1 is a cytogram obtained by a measurement according to an ordinary protocol;

FIG. 2 is a cytogram obtained by the method of the Example according to the present invention;

FIG. 3 is a cytogram obtained from a sample treated with a fluorescence-labeled antibody;

FIG. 4 is a cytogram obtained when a B-CLL specimen is measured;

FIG. 5 is a cytogram obtained when an HCL specimen is measured;

FIG. 6 is a view illustrating a construction of a B-lymphocyte classifying apparatus according to the present invention; and FIG. 7 is a view illustrating one example of an optical system of a flow cytometer used as a detecting section of the B-lymphocyte classifying apparatus according to the present invention.

DETAILED DESCRIPTION OF THE PREFERRED EMBODIMENT

A blood sample refers to a peripheral blood, and represents a sample that is prospected to contain B-lymphocytes.

A lysing reagent is for lysing and removing the erythrocytes in the blood sample that constitute an obstacle against measurement, and for shrinking the B-lymphocytes in the blood sample. The lysing reagent is preferably a reagent containing ammonium chloride. The ammonium chloride is used in an amount sufficient to lyse the erythrocytes, and can be used at a concentration of 5.0 to 20.0 mg/ml. The reagent preferably has a pH value within the range from 6.0 to 8.0, more preferably from 7.0 to 7.5. The pH value can be adjusted by using a suitable acid or alkali. Further, as a countermeasure against coagulation and agglutination, an EDTA salt may be added. The mixing ratio of the blood sample to the lysing reagent is suitably 1:10 to 1:100, preferably 1:20 to 1:30 (blood sample: lysing reagent). The reaction of the blood sample with the lysing reagent can be suitably carried out at a reaction temperature of 4 to 35° C., preferably 15 to 25° C., and for a reaction time of 15 to 60 minutes, preferably 20 to 40 minutes. When the reaction temperature rises, the reaction time can be shortened. Through this step, the erythrocytes in the blood sample are lysed, and the B-lymphocytes are shrunk. In an ordinary lymphocyte subset analysis, a fluorescence-labeled antibody is added to a blood sample for reaction and then, after a lysing reagent is added for reaction at room temperature for about 5 minutes, the measurement is carried out. Alternatively, a lysing reagent is added to a blood sample for reaction at room temperature for about 5 minutes and then, after centrifugation is carried out to remove the supernatant and resuspension is carried out, a fluorescence-labeled antibody is added for reaction and then the measurement is carried out. However, the inventors of the present invention have found out that, by allowing the reaction of the blood sample with the lysing reagent to be carried out for a longer period of time than usual, the B-lymphocytes can be classified without using a fluorescence-labeled antibody. Here, though this step can be carried out manually, an apparatus may be provided with a measurement sample preparing section capable of performing the aforesaid reaction, whereby the blood sample and the lysing reagent can be sent to the measurement sample preparing section by suction means such as a pipette, and a sample prepared in this section can be supplied as a measurement sample.

FIG. 6 illustrates a construction of a B-lymphocyte classifying apparatus according to examples of the present invention. A B-lymphocyte classifying apparatus 100 is constituted with a measurement sample preparing section 101 for performing the aforesaid reaction, a detecting section 102 for measuring a measurement sample prepared in measurement sample preparing section 101, an analyzing section 35 for analyzing a signal detected in detecting section 102, and a displaying section 103 for displaying the results of analysis carried out in analyzing section 35.

FIG. 7 illustrates one example of an optical system of a flow cytometer used as detecting section 102. Referring to FIG. 7, a light emitted from an excited light source (for example, a laser diode) 21 passes through a collimating lens 22 to radiate an orifice section of a sheath flow cell 23. A forward scattered light emitted from a blood cell that is passing through the orifice section after being ejected from a nozzle 6 passes through a condensing lens 24 and a pinhole plate 25 to be incident into a forward scattered light detector (photodiode) 26.

On the other hand, regarding a side scattered light emitted from the blood cell that is passing through the orifice section, the side scattered light passes through a condensing lens 27 and a dichroic mirror 28 to be incident into a side scattered light detector (photomultiplier tube) 29.

A forward scattered light signal that is output from forward scattered light detector 26 and a side scattered light signal that is output from side scattered light detector 29 are amplified by amplifiers 32, 33, respectively, and are input into analyzing section 35.

Here, analyzing section 35 prepares a two-dimensional scattergram using a forward scattered light intensity obtained from the forward scattered light signal and a side scattered light intensity obtained from the side scattered light signal among the input signals, and displays the two-dimensional scattergram on displaying section 103. Also, analyzing section 35 counts the number of dots (the number of particles) within a B-lymphocyte region that is set in the two-dimensional scattergram, and performs desired calculations to display the counting results and the calculation results on displaying section 103.

In addition, in the apparatus 100, a forward low-angle (for example, 0° to 5°) scattered light detector, a forward high-angle (for example, 6° to 20°) scattered light detector, a backward scattered light detector or others is usable, as substitute for above forward scattered light detector 26 or side scattered light detector 29.

A cell in the measurement sample that is flowing through the flow cell is irradiated with a light beam. The light source 21 to be used is not particularly limited, and may be, for example, an argon laser, a He—Ne laser, or a semiconductor laser.

The cell irradiated with a light beam emits scattered light. Among these, for example, a forward scattered light, a forward low-angle (for example, 0° to 5°) scattered light, a forward high-angle (for example, 6° to 20°) scattered light, a side scattered light, a backward scattered light, and others can be used for detection.

Among these scattered light, at least two of these are detected, and a two-dimensional scattergram is prepared using the intensities of the detected scattered light respectively as two axes. A combination of the scattered light preferably includes one (for example, a forward scattered light) that reflects the size of the cell and one (for example, a side scattered light) that reflects the internal information within the cell (for example, granules and nucleus). At this time, when a two-dimensional scattergram is prepared using the forward scattered light intensity as the axis of ordinate and using the side scattered light intensity as the axis of abscissa, the lymphocytes form a cluster at a position having a lower forward scattered light intensity and a lower side scattered light intensity than the other leukocytes. Further, the B-lymphocytes appear at a position having a lower forward scattered light intensity and a higher side scattered light intensity than the other lymphocytes (See FIG. 2). The fact that the cluster appearing at this position represents B-lymphocytes can be confirmed by performing a measurement further using an antibody that recognizes B-lymphocytes, i.e. an anti-CD19 or anti-CD20 antibody labeled with fluorescence.

Subsequently, on the prepared two-dimensional scattergram, a region of a B-lymphocyte cluster is specified (gated), and the number of cells within the specified region is counted. Similarly, when the total lymphocyte cluster is gated on the two-dimensional scattergram and the number of the total lymphocytes is counted, the B-lymphocyte ratio (%) can be calculated from the results of counting the B-lymphocytes in the B-lymphocyte cluster.

EXAMPLES

Example 1

A healthy human being peripheral blood sample (50 μl) treated with an anticoagulation agent (EDTA-2K) was mixed with 1 ml of an ammonium chloride lysing reagent (composition: 89.9 g of $NH_4Cl$, 10.0 g of $KHCO_3$, and 370.0 mg of EDTA4Na are dissolved into 1 liter of distilled water, and adjusted to have a pH value of 7.3 with HCl), and reacted at 20° C. for 5 minutes and 30 minutes. Subsequently, with the use of a flow cytometer (trade name: FACS Calibur, manufactured by Becton, Dickinson and Company.), a forward scattered light intensity and a side scattered light intensity were measured to prepare a two-dimensional scattergram (cytogram). An analysis was carried out using an appended software (trade name: CELLQuest, manufactured by Becton, Dickinson and Company.).

As compared with the case of the measurement according to an ordinary protocol (reaction time: 5 minutes) (See FIG. 1), a new cluster appears at a position lower than the ordinarily confirmed lymphocyte cluster, as shown in FIG. 2, when the measurement is carried out after the reaction is carried out for 30 minutes.

Identification of New Cluster

In order to confirm the derivation of the new cluster that appeared in the aforesaid measurement, a further measurement was carried out using fluorescence-labeled antibodies. The labeled antibodies put to use were as follows.

FITC-labeled anti-CD4 antibody (trade name: CD4 FITC (cat.no.340133), manufactured by Becton, Dickinson and Company.)

PerCP-labeled anti-CD8 antibody (trade name: CD8 PerCP (cat.no.347314), manufactured by Becton, Dickinson and Company.)

FITC-labeled anti-CD19 antibody (trade name: CD19 FITC (cat.no.340864), manufactured by Becton, Dickinson and Company.)

PE-labeled anti-CD56 antibody (trade name: CD56 PE (cat.no.347747), manufactured by Becton, Dickinson and Company.)

FITC-labeled anti-CD14 antibody (trade name: CD14 FITC (cat.no.347493), manufactured by Becton, Dickinson and Company.)

PerCP-labeled anti-CD45 antibody (trade name: CD45 PerCP (cat.no.347464), manufactured by Becton, Dickinson and Company.)

With the use of a healthy human being peripheral blood treated with an anticoagulation agent, mononuclear cells were separated using a specific weight separation reagent (trade name: Lymphoprep, manufactured by AXIS SHIELD Co., Ltd.). To 50 μl thereof, an anti-CD19 fluorescence-labeled antibody and an anti-CD45 fluorescence-labeled antibody were added each in an amount of 10 μl. After the reaction was carried out at 20° C. for 15 minutes, 1 ml of ammonium chloride lysing reagent was further added, and the reaction was carried out at 20° C. for 30 minutes. With the use of FACS Calibur, the forward scattered light intensity, the side scattered light intensity, and the fluorescence intensity were measured. Here, regarding the measurement of fluorescence intensity, red fluorescence or green fluorescence was measured in accordance with each of the labeled antibodies put to use. The analysis was carried out using an appended software (trade name: CELLQuest, manufactured by Becton, Dickinson and Company.). First, a gate for analysis was sectioned as illustrated in FIG. 3, and the ratio of the anti-CD19 fluorescence-labeled antibody positive cells contained within this gate was calculated. Regarding the other labeled antibodies, the analysis was carried out in a similar manner except that each labeled antibody was used instead of the anti-CD19 fluorescence-labeled antibody.

The positiveness ratio of each surface marker of the cells constituting the new cluster obtained in this measurement is shown below.

TABLE 1

| | Surface marker positiveness ratio (%) of new cluster |
|---|---|
| CD4 | 3.2 |
| CD8 | 2.6 |
| CD19 | 82.0 |
| CD56 | 10.6 |
| CD14 | 0.1 |
| Other | 1.6 |

As shown above, almost all the cells constituting the new cluster were found to be CD19-positive cells. Further, in another measurement experiment using a fluorescence-labeled anti-CD20 antibody, the cells in the new cluster were found to be CD20-positive, so that almost all the cells within the new cluster were found to be B-lymphocytes.

Example 2

Measurement of a B-Lymphocytic Disease Patient Specimen

Measurement was carried out using a B-CLL (B-cell chronic lymphocytic leukemia) patient specimen and an HCL (hairy cell leukemia) patient specimen. To 50 μl of a blood sample treated with an anticoagulation agent, 1 ml of ammonium chloride lysing reagent was added and, after the reaction was carried out at 20° C. for 30 minutes, the forward scattered light intensity and the side scattered light intensity were measured using FACS Calibur to prepare a cytogram. The results are shown in FIGS. 4 and 5.

In all of the cases, a different cluster appeared at a position different from the position at which an ordinary lymphocyte cluster appears.

The invention claimed is:
1. A method for classifying B-lymphocytes, comprising the steps of:
   (1) preparing a measurement sample by mixing a blood sample with a lysing reagent to lyse erythrocytes and maintaining a mixture of said lysing reagent and said blood sample for from 15 to 60 minutes to shrink B-lymphocytes in said blood sample;
   (2) flowing said measurement sample through a flow cell of a flow cytometer;

(3) radiating a light beam onto each individual cell in the measurement sample that is flowing through the flow cell;
(4) detecting at least two scattered light emitted from the irradiated cells, wherein said two scattered light are selected from the group consisting of forward scattered light, backward scattered light, and side scattered light;
(5) preparing a two-dimensional scattergram using the detected two scattered light by plotting intensities of the detected two scattered light from each of the cells;
(6) specifying a region of a B-lymphocyte cluster on the two-dimensional scattergram using the detected two scattered light; and
(7) counting the number of B-lymphocytes in the specified region.

2. The method of claim 1, wherein the lysing reagent comprises ammonium chloride.

3. The method of claim 2, wherein the ammonium chloride is present at a concentration of 5 to 20 mg/ml.

4. The method of claim 2, wherein the reagent has a pH value of 6.0 to 8.0.

5. The method of claim 1, wherein a mixing ratio of the blood sample to the lysing reagent in the mixture is 1:10 to 1:100.

6. The method of claim 1, wherein said mixture is maintained for shrinking the B-lymphocytes for from 20 to 20 minutes.

7. The method of claim 1, wherein said two scattered light are the forward scattered light and the side scattered light.

8. The method of claim 1, wherein the forward scattered light includes forward low-angle scattered light and forward high-angle scattered light.

9. A method for classifying B-lymphocytes, comprising the steps of:
(1) preparing a measurement sample by mixing a blood sample with a lysing reagent to lyse erythrocytes and maintaining said lysing reagent and said blood sample for from 15 to 60 minutes to shrink B-lymphocytes in said blood sample;
(2) flowing said measurement sample through a flow cell of a flow cytometer;
(3) radiating a light beam onto each individual cell in the measurement sample that is flowing through the flow cell;
(4) detecting at least two scattered light emitted from the irradiated cells, wherein said two scattered light are selected from the group consisting of forward scattered light, backward scattered light, and side scattered light;
(5) specifying B-lymphocytes on the basis of intensities of the detected two scattered light from each of the cells; and
(6) counting the number of the specified B-lymphocytes.

10. The method of claim 9, wherein the lysing reagent comprises ammonium chloride.

* * * * *